United States Patent [19]

Fujinuma

[11] 3,993,436

[45] Nov. 23, 1976

[54] DYEING LIVE HAIR WITH MELANIN PRECURSORS

[75] Inventor: Yoshimori Fujinuma, Yokohama, Japan

[73] Assignee: Shiseido Co., Ltd., Tokyo, Japan

[22] Filed: Nov. 13, 1974

[21] Appl. No.: 523,272

[30] Foreign Application Priority Data
Dec. 1, 1973  Japan.............................. 48-135874

[52] U.S. Cl. .................................... 8/10.2; 8/11; 8/32; 8/93; 424/71
[51] Int. Cl.² ........................................ A61K 7/13
[58] Field of Search ...................... 8/10.2, 11, 32, 93

[56] References Cited
UNITED STATES PATENTS

| | | | |
|---|---|---|---|
| 2,539,202 | 1/1951 | Peck ..................................... | 8/10.2 |
| 2,875,769 | 3/1959 | Rosmarin et al...................... | 8/10.2 |
| 2,934,396 | 4/1960 | Charle et al. ......................... | 8/10.2 |
| 3,194,734 | 7/1965 | Seemuller et al..................... | 8/10.2 |
| 3,459,198 | 8/1969 | Zemlin et al........................ | 424/71 X |

Primary Examiner—Albert T. Meyers
Assistant Examiner—Vera C. Clarke

[57] ABSTRACT

Hair dye is provided for dyeing hair without causing allergic reaction and with a good coloring effect. This hair dye consists of three hair dyeing compositions, that is, a first dyeing composition including a cutting agent for the cystine-bond of keratin, a second dyeing composition including melanin precursors and boosters for pigmentation, and a third dyeing composition including an oxidizing agent. A process for dyeing hair is also provided in the present specification.

5 Claims, 2 Drawing Figures

DYEING LIVE HAIR WITH MELANIN PRECURSORS

The present invention relates to hair dye for dyeing live hair and other keratinous fibers, which are herein referred to as merely "hair" for brevity's sake, and more particularly the present invention is concerned with a novel hypo-allergenic natural hair dye, the dyeing process of which utilizes the formation mechanism of natural melanin. The present invention also relates to a process for dyeing hair with said hair dye.

Heretofore, hair has been conventionally dyed by permanent hair dyeing processes which are based on the conventional technique comprising the steps of oxidative polymerization of oxidizing azo dye stuffs including mainly p-phenylene diamine by action of hydrogen peroxide in the presence of alkali, and penetrating and fixing the dye stuffs into hair keratin. However, these processes involve some danger. That is, p-phenylene diamine type oxidizing dye which is a main component of the type of hair dyes used in these processes has a tendency to cause allergic reaction in the user.

In order to obviate the problem of allergic reaction various hair dyeing processes which utilize tyrosine, DL-$\beta$-(3,4-dihydroxyphenyl)alanine (hereinafter referred to as "DL-dopa" for brevity's sake) or the like, as a precursor of natural melanin, have been proposed instead of the aforementioned conventional hair dyeing processes. However, these hair dyeing processes have not prevailed as widely as might be expected. This is because there are some associated problems such as the stabilization of the malanin precursor and dyeing conditions to ensure both good dyeing effect and colour fastness.

The object of the present invention is to eliminate the aforementioned problems of the conventional hair dyes and to provide a novel hair dye which is capable of dyeing hair safely, with good colour fastness and with an even distribution of color.

Another object of the present invention is to provide a novel hair dyeing process which enables hair to be dyed with better colour fastness than the conventional process of utilizing the precursor of melanin.

Other objects and advantages of the present invention will be apparent from the following description.

In accordance with the present invention, there is provided a hair dye comprising a first dyeing composition including dithiothreitol and/or dithioerythritol, a second dyeing composition including (a) tyrosine and/or DL-$\beta$-(3,4-dihydroxyphenyl)alanine or its derivatives and (b) at least one compound selected from the group consisting of 5-hydroxyindole, methyl-5,6-dihydroxyindole-2-carboxylate, tyramine, dopamine, 6-hydroxydopamine and pyrocatechol, a third dyeing composition including persulfate and/or tyrosinase which is compounded into said second or third dyeing composition.

In the present hair dye, the first dyeing composition including dithiothreitol (DTT) and/or dithioerythritol (DTE) acts as a cutting agent for the cystine-bond of hair to be dyed and, thus, melanin precursors can be effectively impregnated into keratin and fixed thereto. The melanin precursors used in the present dye are tyrosine and/or DL-dopa or its derivatives, which is compounded into said second dyeing composition. It has now been found that DTT and DTE can reduce the cystine-bond more effectively than mercaptans which are usually employed as the cutting agent for the cystine-bond in the conventional cold waving lotion, that they can be readily rinsed with water from the hair to be treated due to their hydrophilic property derived from the presence of the hydroxyl group, and that they can effectively provide bonding positions of the precursors without disturbing any oxidation reactions. Based on this observation, a novel hair dye utilizing melanin precursors and having a high colour-fixing property can be obtained. For optimum results, it is preferred that the amount of DTT or DTE present in the first dyeing composition be within the range of 0.5 – 3% by weight. When the amount of DTT or DTE is more than 3% by weight, the hair being dyed is hurt and when the amount is less than 0.5% by weight, colour fastness become worse.

Figure 1:
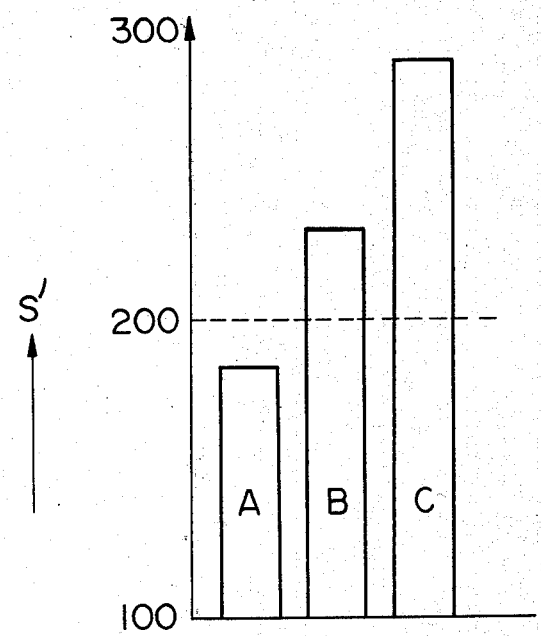
FIG. 1 is an experimental graph showing comparative experimental results of dyeing property by the difference of cutting agents for hair dye.

The above comparative experiments were carried out in the following manner. Wool swatches (white muslin cloth which, after dyeing, is used for colour fastness tests based upon Japanese Industrial Standards L 0803), with a size of 8 cm × 5 cm were dyed with DL-dopa in the presence of tyrosinase at 37° C for 1 hour and, thereafter the wool swatches were shampooed and rinsed with lukewarm water and dried. After drying, the colour fastness of each dyed swatch was measured and the results are shown in FIG. 1. In FIG. 1, A shows the result in the case where the cystine-bond of the wool swatch being tested was not treated by a cutting agent, B shows the result in the case where the wool swatch being tested was pre-treated with 2% by weight of thioglycollic acid solution in aqueous ammonium solution and C shows the result in the case where the wool swatch being tested was pre-treated with 1.7% by weight of dithiothreitol (DTT) solution in aqueous ammonium solution. The measurements of the colour were carried out by using a colour computer (Toshiba CC-1 Type). X, Y and Z values of the dyed wool swatches thus obtained were converted to Hunter's L,$a$ and $b$ chromaticity diagram indicating system and, then, the shade of the dyed cloths ($S'$) was determined by the following equation (1)

$$S' = \sqrt{16(100 - L)^2 + a^2 + b^2} \qquad (1)$$

The values of $S'$ thus obtained can be compared with each other in so far as hue is concerned, and it is true that as the $S'$ value increases, the dyeing property becomes better.

As is apparent from the results shown in FIG. 1., the result of C, which shows the $S'$ value in the case where dithiothreitol (DTT) was employed as a cutting agent was better than the result of B in the case where thioglycollic acid was employed as in the conventional hair dye. Specifically, the $S'$ value of C was 287 and that of B was 231. Of course the result of A, the case where no cutting agent was employed, was the worst of all.

The second dyeing composition according to the present invention comprises melanin precursors such as, for example DL-dopa, tyrosine or the like, and boosters for pigmentation such as, the derivatives of indoles or catechols, which considerably facilitate the fixation of the precursor into the hair. The boosters, according to the present invention, preferably include, for example, 5-hydroxyindole, methyl-5,6-dihydroxyindole-2-carboxylate, dopamine, 6-hydroxydopamine, pyrocatechol, tyramine and their related compounds. Heretofore, 5,6-dihydroxyindole or the like has been used as the lone dyeing component of a hair dye. However, when it is used alone, sufficient hair dyeing effect cannot be obtained, and especially, it is not at all suitable for dyeing dark, stiff hair such as that of Japanese. It has now been found that colour fastness can be significantly increased by using said boosters together with said melanin precursors in a buffer solution of the pH within the range of 6.8 to 8.0. Further, in accordance with the present invention, it is possible to control the shade and the colour of the dyed hair to a fine degree by selecting the compounded substances or the compounding ratio of the melanin precursors and the boosters, and thus, any colour in the range of brown to black can be obtained. For optimum results, it is preferred that the amounts of the precursors and the boosters present in the second dyeing composition be within the range of approximately 0.4 – 0.8% by weight and the range of approximately 0.3 – 3% by weight, respectively.

In the present hair dye, both tyrosinase and persulfate are used as the oxidizing agent. Persulfate used in the present hair dye includes, for example, ammonium persulfate and potassium persulfate. Since tyrosinase and persulfate are used in combination, as the oxidizing agent, in the present invention colour fastness of the present hair dye is considerably improved in comparison with that of the conventional hair dyeing composition using melanin precursors in which only tyrosinase is used as the oxidizing agent. Thus, the cystine-bond which is cut by the action of DTT or DTE is effectively recombined and the dyed hair undergoes relatively little damage. Persulfate is compounded into the third dyeing composition of the present invention, and tyrosinase can be compounded into the second or the third dyeing composition of the present invention. For optimum results, it is preferred that the amount of said persulfate present in the third dyeing composition be within the range of approximately 1% to 10% by weight, and that the amount of said tyrosinase present in the second or third dyeing composition, be within the range of approximately 0.1% to 0.5% by weight.

The present invention also includes a hair dyeing process which comprises the steps of treating hair to be dyed with said first dyeing composition, then applying thereto said second dyeing composition and thereafter, embrocating the hair with said third dyeing composition.

In accordance with the preferred embodiment of the present invention, hair to be dyed is firstly treated with an aqueous ammonium solution of the first dyeing composition of the present invention for 10–15 minutes, the composition comprising DTT and/or DTE, and a humectant, both dissolved in ammonium solution. The humectant preferably includes sorbitol, 1,2-propylene glycol, polyethylene glycol, glycerol or the like, and it is preferred that the amount of the humectant in the first dyeing composition be within the range of approximately 0.5–5% by weight. By treating hair to be dyed with the first dyeing composition, the cystine-bond of the hair is effectively reduced. Secondly, the second dyeing composition in a phosphate buffer solution of pH 6.8 to 8.0 is applied to the hair for a sufficient time, for example about 30 – 60 minutes. During this application, a penetrating agent such as polyoxyethylene (15)-nonyl-phenyl-ether, polyoxyethylene (20)-octylphenyl-ether, polyoxyethylene (20)-sorbitan-monolaurate or polyoxyethylene (40)-sorbitan-monostearate is preferably added into the second dyeing composition in order to facilitate the impregnation of the composition into the hair. For this purpose, it is also effective to mechanically rub the composition into the hair. The amount of the penetrating agent is preferably within the range of 2% and 3% by weight based upon the weight of the second dyeing composition. Further, into the second composition, in order to prevent the composition from dripping from the hair, a thickening agent such as water-soluble resins such as hydroxyethyl cellulose is compounded to give suitable viscosity to the composition. Finally, the hair is embrocated with the third dyeing composition which comprises tyrosinase and persulfate such as, for example, ammonium persulfate or potassium persulfate. The tyrosinase and persulfate are compounded just before the third dyeing composition is to be used. The hair thus treated with the third composition is allowed to stand for about 10 – 15 minutes and, thereafter, the hair is shampooed and rinsed with water. The tyrosinase may be compounded into the third composition or it may be compounded into the second composition just before the composition is used.

The present invention now will be further illustrated by the following examples. However, it should be understood that these are given merely to explain and not to limit the invention and that numerous changes may be made without departing from the spirit and the scope of the invention as hereinafter claimed.

In the examples, each aqueous ammonium solution to be employed is a 8.5% by weight aqueous solution which is prepared by diluting a 29% by weight aqueous ammonium solution with pure water. Further, the tyrosinase to be used in each example is 500 units/mg of mushroom tyrosinase, and it is added to the second of the thrid composition to activate the composition just before the composition is used.

EXAMPLE 1

The following three dyeing compositions were respectively prepared.

The first dyeing composition was prepared by dissolving the following ingredients in 100 ml of aqueous ammonium solution:

| | |
|---|---|
| dithiothreitol | 1.0 g |
| propylene glycol | 0.5 g |
| ethylenediaminetetraacetic acid (as sodium salt) | 0.05 g |

The second dyeing composition was prepared by dissolving the following ingredients in 100 ml of a phosphate buffer solution of pH 6.8 :

| | |
|---|---|
| DL - dopa | 0.4 g |
| L - tyrosine | 0.01 g |
| 5-hydroxyindole | 0.5 g |
| tyrosinase* | 0.2 g |
| hydroxyethylcellulose | 0.3 g |

*tyrosinase was dissolved just before the second dyeing composition was used for treating the hair to be dyed.

The third dyeing composition was prepared by dissolving 3.0g of ammonium persulfate in 50 ml of pure water.

The hair was treated with the first dyeing composition at ambient temperature for 15 minutes and, thereafter, the treated hair was shampooed and rinsed with lukewarm water. Then, the hair was treated with the second dyeing composition at ambient temperature for 60 minutes. Further, the treated hair was embrocated with the third dyeing composition for 10 minutes. Thus, the hair was dyed black.

EXAMPLE 2

The first dyeing composition was prepared by dissolving the following ingredients in 100 ml of aqueous ammonium solution:

| | |
|---|---|
| dithiothreitol | 2.0 g |
| propylene glycol | 5.0 g |
| ethylenediaminetetraacetic acid (as sodium salt) | 0.1 g |

The second dyeing composition was prepared by dissolving the following ingredients in 100 ml of a phosphate buffer solution of pH 7.0 :

| | |
|---|---|
| DL-dopa | 0.4 g |
| 6-hydroxydopamine hydrochloride | 0.5 g |
| tyrosinase* | 0.3 g |
| hydroxyethylcellulose | 0.5 g |

*tyrosinase was dissolved just before the second dyeing composition was used for treating the hair to be dyed.

The third dyeing composition was prepared by dissolving 3.0 g of ammonium persulfate in 50 ml of pure water.

The hair was treated for 5 minutes with the first dyeing composition obtained above and, thereafter, the treated hair was shampooed and rinsed with lukewarm water. Then the hair was treated with the second dyeing composition for 60 minutes and, thereafter, the hair was embrocated with the third dyeing composition for 10 minutes. Thus, the hair was dyed black. In the above hair dyeing procedure, by changing the compounding molar ration of DL-dopa to 6-hydroxydopamine hydrochloride in the second dyeing composition, from 1 : 1 to 2 : 1 the hair was dyed from a reddish brown to a dark brown.

EXAMPLE 3

The first dyeing composition was prepared by dissolving the following ingredients in 100 ml of aqueous ammoniun solution:

| | |
|---|---|
| dithiothreitol | 0.5 g |
| dithioerythritol | 1.0 g |
| propylene glycol | 2.0 g |
| ethylenediaminetetraacetic acid (as sodium salt) | 0.1 g |

The second dyeing composition was prepared by dissolving the following ingredients in 100 ml of a phosphate buffer solution of pH 8.0 :

| | |
|---|---|
| DL-dopa | 0.4 g |
| dopamine hydrochloride | 3.0 g |
| tryosinase* | 0.4 g |
| hydroxyethylcellulose | 0.5 g |

*tyrosinase was dissolved just before the second dyeing composition was used for treating the hair to be dyed.

The third dyeing composition was prepared by dissolving 3.0 g of ammonium persulfate in 50 ml of pure water.

The hair was treated with the first dyeing composition for 10 minutes and, thereafter, the treated hair was shampooed and rinsed with lukewarm water. Then, the hair was treated with the second dyeing composition for 60 minutes, and, further, the hair was embrocated with the third dyeing composition for 10 minutes. Thus, the hair was dyed black. In the above dyeing process, by changing the compounding ration of DL-dopa and dopamine in the second dyeing composition, the colour of the hair was dyed from a black to a dark brown.

EXAMPLE 4

The first dyeing composition was prepared by dissolving the following ingredients in 100 ml of aqueous ammonium solution:

| | |
|---|---|
| dithiothreitol | 1.7 g |
| propylene glycol | 2.0 g |
| ethylenediamine-tetraacetic acid (as sodium salt) | 0.1 g |

The second dyeing composition was prepared by dissolving the following ingredients in 100 ml of a phosphate buffer solution of pH 8.0 :

| | |
|---|---|
| DL-dopa | 0.4 g |
| tyramine hydrochloride | 1.5 g |
| tyrosinase | 0.3 g |
| hydroxyethylcellulose | 0.5 g |

The third dyeing composition was prepared by dissolving 3.0 g of potassium persulfate in 50 ml of pure water.

The hair was dyed by using these three dyeing compositions in the same manner as that of Example 3 and, thus, the treated hair was dyed dark brown.

EXAMPLE 5

The first dyeing composition was prepared by dissolving the following ingredients in 100 ml of aqueous ammonium solution:

| | |
|---|---|
| dithioerythritol | 1.7 g |
| propylene glycol | 2.0 g |
| ethylenediaminetetraacetic acid (as a sodium salt) | 0.1 g |

The second dyeing composition was prepared by dissolving the following ingredients in 100 ml of a phosphate buffer solution of pH 6.8 :

| | |
|---|---|
| DL-dopa | 0.4 g |
| 5-hydroxyindole | 0.2 g |
| pyrocatechol | 0.2 g |

| | hydroxyethylcellulose | 0.5 g |
|---|---|---|

The third dyeing composition was prepared by dissolving 0.4 g of tyrosinase and 3.0 g of ammonium persulfate in 50 ml of pure water.

The hair was treated for 10 minutes with the first dyeing composition prepared above and, thereafter, the treated hair was shampooed and rinsed with lukewarm water. Then, the second dyeing composition and the third dyeing composition were mixed together and, immediately, the mixture was sprinkled over the hair and, thereafter, the hair was embrocated for one hour. Thus, the hair was dyed black.

EXAMPLE 6

The first dyeing composition was prepared by dissolving the following ingredients in 100 ml of aqueous ammonium solution:

| | | |
|---|---|---|
| | $\beta$-mercaptoethanol | 2.0 g |
| | dithiothreitol | 0.5 g |
| | propylene glycol | 5.0 g |
| | ethylenediaminetetraacetic acid (as sodium salt) | 0.1 g |

The second dyeing composition was prepared by dissolving the following ingredients in 100 ml of a phosphate buffer solution of pH 8.0:

| | |
|---|---|
| DL-dopa methylester hydrochloride | 0.6 g |
| pyrocatechol | 0.3 g |
| methyl-5,6-dihydroxyindole-2-carboxylate | 0.01 g |
| hydroxyethylcellulose | 0.5 g |

The third dyeing composition was prepared by dissolving 0.3 g of tyrosinase and 3.0 g of ammonium persulfate in 50 ml of pure water.

The hair was treated with these three dyeing compositions in the same manner as that of Example 5 and, thus, the treated hair was dyed brown.

EXAMPLE 7

This example illustrates the effect of the compounding ratio of the melanin precursor and the boosters for pigmentation on the dyed colour.

Each of eleven wool swatches (white muslin cloth used for colour fastness tests) with a size of 8 cm × 5 cm was pretreated with a 0.5% by weight DTT solution in a 8.5% by weight aqueous ammonium solution for 10 minutes. Then, each of the treated wool swatches was dyed with a different second dyeing compositions as shown in Table 1, at 37° C for 50 minutes in the presence of 10 mg of tyrosinase (500 units/mg) and, thereafter, each of the treated wool swatches was further dyed by adding 0.1 g of ammonium persulfate for 10 minutes. Each of the dyed wool swatches was soaked in a 10% shampooing solution for 5 minutes and shaken for 2 minutes and, thereafter, each of the dyed wool swatches was washed well with lukewarm water the temperature of which was about 40° C.

Table 1

| Run No. | Dopa (mg) | 5-hydroxyindole (mg) | Pyrocatechol (mg) |
|---|---|---|---|
| 1 | 50 | 0 | — |
| 2 | 40 | 10 | — |
| 3 | 30 | 20 | — |
| 4 | 20 | 30 | — |
| 5 | 10 | 40 | — |
| 6 | 0 | 50 | — |
| 7 | 40 | — | 10 |
| 8 | 30 | — | 20 |
| 9 | 20 | — | 30 |
| 10 | 10 | — | 40 |
| 11 | 0 | — | 50 |

Note: The ingredients listed in Table 1 were dissolved in 15 ml of a buffer solution of phosphoric acid (pH 6.8).

After drying, the colour of each dyed wool swatch was measured by using a colour computer. X, Y and Z values of the dyed wool swatches thus measured were converted into Hunter's L, a and b chromaticity diagram indicating system and, then, the converted values of a and b were plotted in FIG. 2. Each number plotted in FIG. 2 indicates the same run No. in Table 1.

Figure 2:
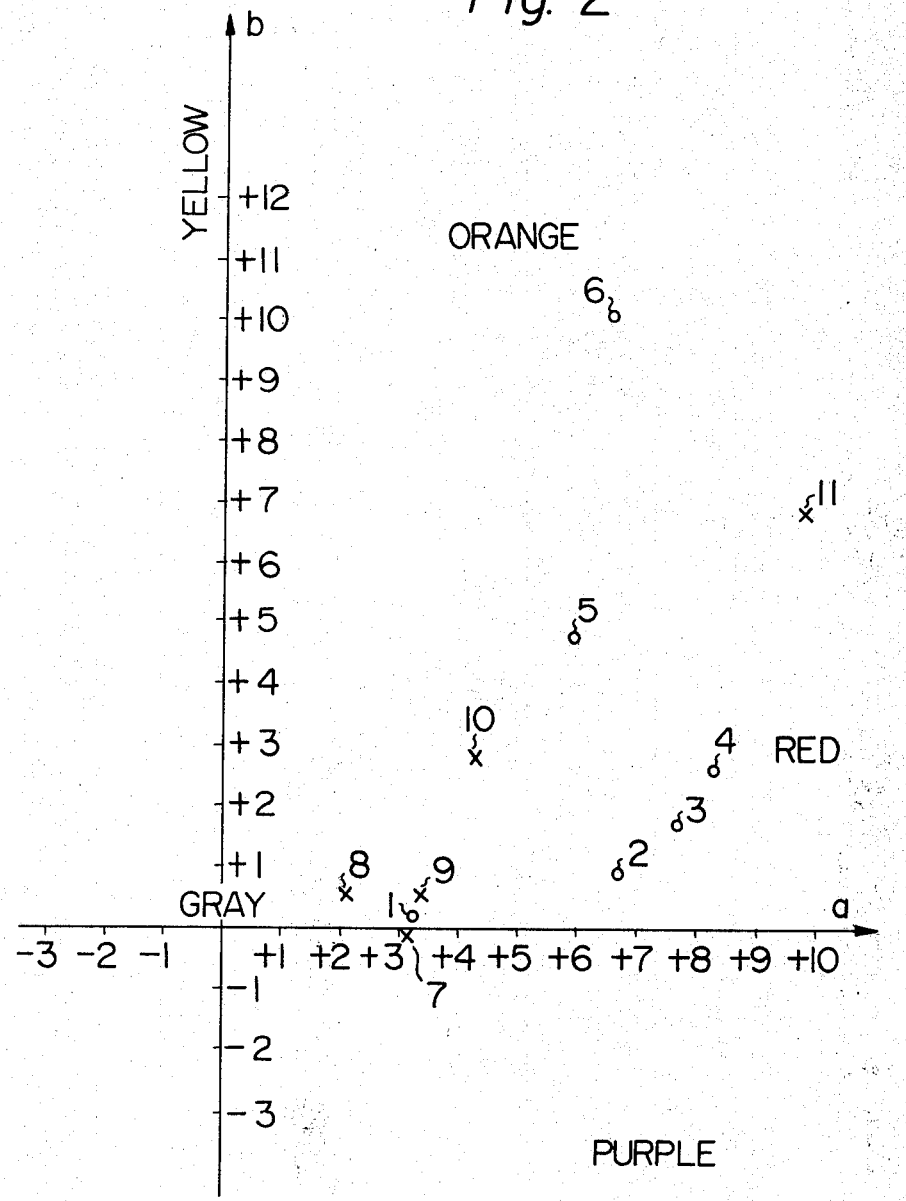
FIG. 2 is a plotted diagram of colour fastness tests on wool swatches.

As shown in FIG. 2, in the case where the second dyeing composition of the present invention containing dopa and 5-hydroxyindole in a phosphate buffer solution was used, i.e., run No. 1 through No. 6, as the compounded amount of 5-hydroxyindole increased against the compounded amount of dopa, it was observed that the hue of the dyed wool swatch went from a gray through orange to red. On the other hand, in the case where the second dyeing composition containing dopa and pyrocatechol was used, i.e. run No. 7 through No. 11, as the compounded amount of pyrocatechol increased against the compounded amount of dopa, it can be observed from FIG. 2 that when the colour computer is used although the chroma of the dyed wool swatches is varied, the hue remains similar. However, upon visual inspection the shade of the dyed wool swatch varies from a black to a dark-red.

What we claim is:

1. A hair dye comprising
   0.5–3% by weight of a first dyeing component which is a compound selected from the group consisting of dithiothreitol and dithioerythritol;
   a second dyeing component which comprises 0.4–8% by weight of (a) a compound selected from the group consisting of tyrosine, DL-$\beta$-(3,4-dihydroxyphenyl)alanine, and the methyl ester of the latter compound, and (b) 0.3–3% by weight of a compound selected from the group consisting of 5-hydroxyindole, methyl-5,6-dihydroxyindole-2-carboxylate, tyramine, dopamine, 6-hydroxydopamine and pyrocatechol;
   1–10% by weight of a third dyeing component which is a persulfate selected from the group consisting of ammonium persulfate and potassium persulfate, and; said hair dye further comprising 0.1–5% by weight of tyrosinase in combination with said second or third dyeing component; and said first, second and third components being in combination with an aqueous carrier.

2. The hair dye as claimed in claim 1 wherein said and first component is present in an aqueous ammonium solution.

3. The hair dye as claimed in claim 1 wherein said second dyeing component is in a phosphate buffer solution of pH 6.8 to 8.0.

4. A hair dyeing process comprising the steps of:
   i. treating hair to be dyed with an aqueous mixture of 0.5–3% by weight of a first dyeing component which is a compound selected from the group consisting of dithiothreitol and dithioerythritol;
   ii. applying thereto an aqueous mixture of a second dyeing component which comprises 0.4–0.8% by weight of
      a. a compound selected from the group consisting of tyrosine, DL-$\beta$-(3,4-dihydroxyphenyl)alanine and the methyl ester of the latter compound and (b) 0.3–3% by weight of a compound selected from the group consisting of 5-hydroxyindole, methyl-5,6-dihydroxyindole-2-carboxylate, tyramine, dopamine, 6-hydroxydopamine and pyrocatechol; and
   iii. embrocating the hair with 1–10% by weight of an aqueous mixture of a third dyeing component which is a persulfate selected from the group consisting of ammonium persulfate and potassium persulfate, and 0.1–0.5% by weight tyrosinase.

5. A hair dyeing process comprising the steps of:
   i. treating hair to be dyed with an aqueous mixture of 0.5–3% by weight of a first component which is a compound selected from the group consisting of dithiothreitol and dithioerythritol;
   ii. applying thereto an aqueous mixture of a second component which comprises
      a. 0.4–0.8% by weight of a compound selected from the group consisting of tyrosine, DL-$\beta$-(3,4-dihydroxyphenyl)alanine and the methyl ester of the latter compound and (b) 0.3–3% by weight of a compound selected from the group consisting of 5-hydroxyindole, methyl-5,6-dihydroxyindole-2-carboxylate, tyramine, dopamine, 6-hydroxydopamine and pyrocatechol and 0.1–0.5% by weight of tyrosinase, and;
   iii. embrocating the hair with 1–10% by weight of an aqueous mixture of a third component containing a persulfate selected from the group consisting of ammonium persulfate and potassium persulfate.

* * * * *

UNITED STATES PATENT OFFICE
CERTIFICATE OF CORRECTION

PATENT NO. : 3,993,436
DATED : November 23, 1976
INVENTOR(S) : Yoshimori Fujinuma It is certified that error appears in the above-identified patent and that said Letters Patent are hereby corrected as shown below:

Col. 8, line 49, change "0.4-8%" to --0.4-0.8%--.

Col. 8, line 61, change "0.1-5%" to --0.1-0.5%--.

Col. 8, line 67, delete "and".

Signed and Sealed this

Fourteenth Day of November 1978

[SEAL]

Attest:

RUTH C. MASON
Attesting Officer

DONALD W. BANNER
Commissioner of Patents and Trademarks